United States Patent
Kato et al.

(10) Patent No.: US 10,774,306 B2
(45) Date of Patent: Sep. 15, 2020

(54) METHOD FOR INCREASING IMMUNOPOTENTIATING ACTIVITY OF LACTIC ACID BACTERIA

(71) Applicant: Kirin Holdings Kabushiki Kaisha, Nakano-ku, Tokyo (JP)

(72) Inventors: Yukiko Kato, Tokyo (JP); Masaya Kanayama, Tokyo (JP)

(73) Assignee: Kirin Holdings Kabushiki Kaisha, Tokyo (JP)

(*) Notice: Subject to any disclaimer, the term of this patent is extended or adjusted under 35 U.S.C. 154(b) by 51 days.

(21) Appl. No.: 15/773,388

(22) PCT Filed: Nov. 7, 2016

(86) PCT No.: PCT/JP2016/082907
§ 371 (c)(1),
(2) Date: May 3, 2018

(87) PCT Pub. No.: WO2017/082181
PCT Pub. Date: May 18, 2017

(65) Prior Publication Data
US 2018/0312799 A1 Nov. 1, 2018

(30) Foreign Application Priority Data
Nov. 10, 2015 (JP) .................. 2015-220653

(51) Int. Cl.
| | | |
|---|---|---|
| A61K 35/744 | (2015.01) | |
| A23L 33/135 | (2016.01) | |
| C12N 1/20 | (2006.01) | |
| C12N 1/38 | (2006.01) | |
| C12R 1/46 | (2006.01) | |

(52) U.S. Cl.
CPC .............. *C12N 1/20* (2013.01); *A23L 33/135* (2016.08); *C12N 1/38* (2013.01); *C12R 1/46* (2013.01); *A61K 35/744* (2013.01)

(58) Field of Classification Search
None
See application file for complete search history.

(56) References Cited

U.S. PATENT DOCUMENTS

| | | |
|---|---|---|
| 5,556,785 A | 9/1996 | Kishida |
| 2013/0302380 A1 | 11/2013 | Fujiwara et al. |
| 2017/0189458 A1 | 7/2017 | Kanayama et al. |

FOREIGN PATENT DOCUMENTS

| | | |
|---|---|---|
| EP | 1920774 A1 | 5/2008 |
| JP | 05-097689 A | 4/1993 |
| JP | 06-206826 A | 7/1994 |
| JP | 08-99887 A | 4/1996 |
| JP | 2002-080364 A | 3/2002 |
| JP | 2007-204488 A | 8/2007 |
| JP | 2007-302628 A | 11/2007 |
| JP | 2011-037888 A | 2/2011 |
| JP | 2012-184261 A | 9/2012 |
| WO | WO 2007/013613 A1 | 2/2007 |
| WO | WO 2012/091081 A1 | 7/2012 |
| WO | WO 2015/182735 A1 | 12/2015 |

OTHER PUBLICATIONS

Pessione E. Front. Cell Infect. Microbiol. 2: 1-15, 2012.*
International Search Report dated Jan. 31, 2017, in PCT/JP2016/082907.
Fujiwara et al., "Product Innovation: Development of lactic acid bacteria activating plasmacytoid dendritic cells controlling protection from viral infection," Kagaku to Seibutsu, Aug. 2015, 53(9):626-632, with partial English translation, 5 pages.
Kuwana et al., "Evaluation of cytotoxicity of emulsifying agent on *Bacillus subtilis*," Abstracts of Annual Meeting of Pharmaceutical Society of Japan, 2011, 131(3):217, 30P-0666, with partial English translation.
Third Party submission dated Feb. 4, 2020, in JP 2015-220653.
Tobita et al., "The Antiallergic Effects and Acute Toxicity of *Lactobacillus crispatus* KT-11 Cultured in Food Grade Medium," Journal of Agriculture and Food Chemistry, 2010, 58:6498-6502.

\* cited by examiner

*Primary Examiner* — Sarvamangala Devi
(74) *Attorney, Agent, or Firm* — Foley & Lardner LLP (57) ABSTRACT

A lactic acid bacterium having increased immunopotentiating activity with being mixed with no ester compound of polyol and a fatty acid is provided. A method for producing a lactic acid bacterium whose immunopotentiating activity is increased without coexisting with ester compound of polyol and a fatty acid, comprising: contacting a lactic acid bacterial immunopotentiating activity-increasing composition comprising an ester compound of a polyol and a fatty acid as an active ingredient with a lactic acid bacterium having immunopotentiating activity and then washing the lactic acid bacterium to remove the lactic acid bacterial immunopotentiating activity-increasing composition.

9 Claims, 5 Drawing Sheets

Fig. 5

METHOD FOR INCREASING IMMUNOPOTENTIATING ACTIVITY OF LACTIC ACID BACTERIA

CROSS-REFERENCE TO RELATED APPLICATIONS

This application is a National Stage application of PCT/JP2016/082907, filed Nov. 7, 2016, which claims priority from Japanese application JP 2015-220653, filed Nov. 10, 2015.

TECHNICAL FIELD

The present invention relates to a method for increasing immunopotentiating activity of lactic acid bacteria using a lactic acid bacterial immunopotentiating activity-increasing composition that increases immunopotentiating activity of lactic acid bacteria having immunopotentiating activity.

BACKGROUND ART

A cold and influenza are diseases mainly caused by infection with a virus and resulting in poor physical conditions. Experiencing the outbreak of the new influenza, people are seeking for beverages and foods having the immunopotentiating effect for preventing a cold and influenza. Lactic acid strains such as *Lactococcus lactis* subsp. *lactis* JCM5805 (see Patent Literature 1), *Lactobacillus bulgaricus* OLL1073R-1 (see Patent Literature 2), *Enterococcus faecalis* (see Patent Literature 3), *Lactobacillus brevis* subsp. *coagulans* (see Patent Literature 4), and *Lactococcus gasseri* (see Patent Literature 5) have been known to exhibit the immunopotentiating effect and used in plural beverages and foods. However, to have an adequate effect of such bacteria, an amount of the bacteria exceeding a certain amount has been required and addition of a large amount of such bacteria in a beverage has resulted in decrease in the commercial value due to, for example, production of precipitates and/or flavor deterioration. Therefore, a method for having an adequate effect of such a lactic acid bacterium in a small quantity has been desired. Methods for increasing the immunopotentiating effect of lactic acid bacteria and products having an increased immunological effect have been reported recently. Examples include beverages and foods for increasing immunity, comprising a combination of a lactic acid bacterium and grains of a Poaceae plant (see Patent Literature 5); a composition comprising fucoidan or a fucoidan hydrolysate and an immuno-stimulating material (see Patent Literature 6); a culture obtained by inoculating a lactic acid bacterium into a medium containing a processed asparagus product for lactic fermentation (see Patent Literature 7); a method involving using ascorbic acid and a lactic acid bacterium in combination (see Patent Literature 8); and a method involving combining vitamin E and a lactic acid bacterium (see Patent Literature 9).

CITATION LIST

Patent Literature

Patent Literature 1: International Publication No. WO2012/091081
Patent Literature 2: JP Patent Publication (Kokai) No. 2011-37888 A
Patent Literature 3: JP Patent Publication (Kokai) No. 5-97689 A (1993)
Patent Literature 4: JP Patent Publication (Kokai) No. 6-206826 A (1994)
Patent Literature 5: JP Patent Publication (Kokai) No. 2012-184261 A
Patent Literature 6: International Publication No. WO2007/013613
Patent Literature 7: JP Patent Publication (Kokai) No. 2007-302628 A
Patent Literature 8: JP Patent Publication (Kokai) No. 2007-204488 A
Patent Literature 9: JP Patent Publication (Kokai) No. 2002-080364 A

SUMMARY OF INVENTION

Technical Problem

However, grains of a Poaceae plant are a granular material and produce precipitates when used in a beverage or food. The methods using asparagus requires fermentation of a processed asparagus product with a lactic acid bacterium, taking efforts and cost, as well as producing a problem of flavor. Fucoidan is a high molecular weight polysaccharide with a high viscosity and therefore difficult to handle, and a fucoidan hydrolysate is a mixture of plural oligosaccharides and produces a problem of flavor. Ascorbic acid is vulnerable to heat and vitamin E is liposoluble and difficult to handle. Moreover, the aforementioned methods and the like are methods for increasing production of interferon γ and nothing is described on type I interferon, which is most important for the prevention of viral infections.

Therefore, a water-soluble ingredient that synergistically increases the immunopotentiating activity of lactic acid bacteria and has no large effect on the flavor can reduce the amount of the lactic acid bacteria to be used while maintaining its activity, and, as a result, increase the scope of the development of compositions containing lactic acid bacteria. Compositions having a strong protective effect against viral infections can be provided by focusing particularly on type I interferon for the immunopotentiating activity.

The present inventors have previously developed a lactic acid bacterial immunopotentiating activity-increasing composition that increases immunopotentiating activity of lactic acid bacteria having immunopotentiating activity, wherein addition of a small amount of the lactic acid bacterial immunopotentiating activity-increasing composition can produce an adequate effect of the lactic acid bacteria; and a method for increasing the immunopotentiating activity of lactic acid bacteria using the composition. In the method, immunopotentiating activity of lactic acid bacteria is increased by contacting an ester compound of a polyol and a fatty acid with lactic acid bacteria. In the method, the ester compound of a polyol and a fatty acid is contacted with the lactic acid bacteria and the resulting lactic acid bacterial composition in which the ester compound of a polyol and a fatty acid is still mixed is used as a medicine or a food or drink.

Ester compounds of a polyol and a fatty acid have the emulsifying activity and sometimes caused agglutination of lactic acid bacteria.

Therefore, an object of the present invention is to provide lactic acid bacteria whose immunopotentiating activity is increased without coexisting with ester compound of a polyol and a fatty acid.

Solution to Problem

The present inventors have studied diligently to achieve the aforementioned object and have found, as a result, that ester compounds of a polyol and a fatty acid have an effect of increasing the immunopotentiating activity of lactic acid bacteria. The present inventors have examined whether the immunopotentiating activity of lactic acid bacteria is increased when the lactic acid bacteria were contacted with an ester compound of polyol and a fatty acid and then the lactic acid bacteria were washed to remove the ester compound of polyol and a fatty acid to avoid incorporating an ester compound of a polyol and a fatty acid having emulsifying activity in a composition containing a lactic acid bacterium, and found that the immunopotentiating activity of lactic acid bacteria was increased even after the washing and that compositions containing such lactic acid bacteria are available as lactic acid bacterium-containing compositions, thereby completing the present invention.

Accordingly, the present invention is as follows.

[1] A method for producing a lactic acid bacterium whose immunopotentiating activity is increases without coexisting with ester compound of polyol and a fatty acid, comprising: contacting a lactic acid bacterial immunopotentiating activity-increasing composition comprising an ester compound of a polyol and a fatty acid as an active ingredient with a lactic acid bacterium having immunopotentiating activity and then washing the lactic acid bacterium to remove the lactic acid bacterial immunopotentiating activity-increasing composition.

[2] The method according to [1], wherein the polyol is selected from the group consisting of monoglycerol, polyglycerol, and sucrose.

[3] The method according to [1] or [2], wherein the fatty acid is selected from the group consisting of caprylic acid, capric acid, lauric acid, myristic acid, palmitic acid, stearic acid, oleic acid, and behenic acid.

[4] The method according to any one of [1] to [3], wherein the ester compound of a polyol and a fatty acid is not modified with any organic acid.

[5] The method according to any one of [1] to [4], wherein the ratio of the concentration of the ester compound of a polyol and a fatty acid contacted with the lactic acid bacterium having immunopotentiating activity to the concentration of the lactic acid bacterium is in the range of 0.002 to 8:1.

[6] The method according to any one of [1] to [5], wherein the lactic acid bacterium having immunopotentiating activity is a lactic acid bacterium capable of inducing interferon production from an interferon-producing cell.

[7] The method according to any one of [1] to [6], wherein the lactic acid bacterium having immunopotentiating activity is selected from the group consisting of *Lactococcus garvieae, Lactococcus lactis* subsp. *cremoris, Lactococcus lactis* subsp. *lactis, Lactococcus lactis* subsp. *hordniae, Leuconostoc lactis*), *Pediococcus damnosus, Streptococcus thermophilus, Lactobacillus brevis* subsp. *coagulans*, and *Enterococcus faecalis*.

[8] The method according to [6] or [7], wherein the lactic acid bacterium having immunopotentiating activity is *Lactococcus lactis* JCM5805.

The description of the present application encompasses the contents disclosed in JP Patent Application No. 2015-220653, which the priority of the present application is based on.

Advantageous Effects of Invention

Ester compounds of a polyol and a fatty acid increase the immunopotentiating activity of lactic acid bacteria having immunopotentiating activity. Accordingly, coexistence of lactic acid bacteria with an ester compound of a polyol and a fatty acid, for example, in culture increases the effect of the lactic acid bacteria on interferon-producing cells to induce the interferon production. This immunopotentiating activity is present after lactic acid bacteria are cultured in the presence of an ester compound of polyol and a fatty acid and then washed to remove the ester compound of a polyol and a fatty acid. Moreover, if lactic acid bacteria are cultured in the presence of an ester compound of a polyol and a fatty acid and then washed to increase the immunopotentiating activity of the lactic acid bacteria, then the possible range of ratios of the lactic acid bacteria and the ester compound of a polyol and a fatty acid at the time of culturing the lactic acid bacteria in the presence of the ester compound of a polyol and a fatty acid is large, providing the effect in a wide range.

Lactic acid bacteria having increased immunopotentiating activity obtained in the method according to the present invention can be used as an active ingredient in a lactic acid bacterium-containing composition having immunopotentiating activity.

DESCRIPTION OF EMBODIMENTS

The present invention will be described in detail below.

The present invention relates to a method for increasing immunopotentiating activity of a lactic acid bacterium, comprising: contacting a lactic acid bacterial immunopotentiating activity-increasing composition comprising an ester compound of a polyol and a fatty acid as an active ingredient with a lactic acid bacterium and then washing the lactic acid bacterium to remove the ester compound of a polyol and a fatty acid.

An ester compound of a polyol and a fatty acid consists of a hydrophilic moiety and a lipophilic moiety and has a structure in which a polyol, which is the hydrophilic moiety, and a fatty acid, which is the lipophilic moiety, are linked by an ester bond. The polyol in the ester compound of a polyol and a fatty acid is an alcohol having 2 or more hydroxyl groups in the molecule, wherein the number of hydroxyl groups is, for example, 2 to 15, but not limited. The polyol may have an aldehyde group and/or a ketone group. A polyol having an aldehyde group and/or a ketone group is sugar or a sugar alcohol.

The number of carbon atoms in the polyol contained in a lactic acid bacterial immunopotentiating activity-increasing composition used in the method for increasing the potentiating activity of a lactic acid bacterium according to the present invention is 2 to 20 and preferably 3 to 20. The greater molecular weight is preferred for the polyol and the molecular weight is 50 or more, preferably 60 or more, and more preferably 90 or more. In the comparison of the increasing effect of, for example, sucrose (molecular weight 342), triglycerol (molecular weight 240), diglycerol (molecular weight 166), and monoglycerol (molecular weight 92), the effect is greater in this order.

Examples of the polyol include ethylene glycol ($C_2H_6O_2$) and propylene glycol ($C_3H_8O_2$), which are dihydric alcohol; monoglycerol ($C_3H_8O_3$), which is trihydric alcohol; diethylene glycol ($C_4H_{10}O_3$), which is tetrahydric alcohol; diglycerol ($C_6H_{14}O_5$), which is pentahydric alcohol; triglycerol ($C_9H_{20}O_7$); and polyglycerol. Polyethyleneglycol, which has a large number of hydroxyl groups, may be also used. Examples of the polyol that is sugar include sucrose ($C_{12}H_{22}O_{11}$). Examples of the polyol that is a sugar alcohol include xylitol ($C_5H_{12}O_5$), sorbitol ($C_6H_{14}O_6$), mannitol ($C_6H_{14}O_6$), and sorbitan. Among these, polyglycerol or sucrose is preferred.

When an organic acid such as succinic acid or tartaric acid is linked to the polyol, the immunopotentiating activity-increasing effect of lactic acid bacteria is decreased. Polyols to which an organic acid is linked, however, have the detectable immunopotentiating activity-increasing effect and can therefore be used. Polyols to which no organic acid is linked are preferably used.

The number of carbon atoms in the fatty acid contained in a lactic acid bacterial immunopotentiating activity-increasing composition used in the method for increasing the potentiating activity of the lactic acid bacterium according to the present invention is 8 to 30. The fatty acid includes both the unsaturated fatty acid and the saturated fatty acid. More specifically, examples include caprylic acid (octanoic acid) (C8), capric acid (decanoic acid) (C10), lauric acid (dodecanoic acid) (C12), myristic acid (tetradecanoic acid) (C14), pentadecylic acid (pentadecanoic acid) (C15), palmitic acid (hexadecanoic acid) (C16), margaric acid (heptadecanoic acid) (C17), oleic acid (C18), stearic acid (octadecanoic acid) (C18), arachidic acid (icosanoic acid) (C20), behenic acid (docosanoic acid) (C22), lignoceric acid (tetradocosanoic acid) (C24), cerotic acid (hexadocosanoic acid) (C26), montanic acid (octadocosanoic acid) (C26), and melissic acid (C28). Among these, caprylic acid, capric acid, lauric acid, myristic acid, palmitic acid, stearic acid, and behenic acid may be preferably used. Among these, palmitic acid, stearic acid, or oleic acid is preferred.

A lactic acid bacterial immunopotentiating activity-increasing composition used in the method for increasing the potentiating activity of a lactic acid bacterium according to the present invention is an aforementioned composition comprising an ester compound in which a hydroxyl group of the polyol and a carboxyl group of the fatty acid(s) described above are linked by an ester bond as an active ingredient.

The number of the fatty acid(s) linked to 1 molecule of the polyol in the ester compound of a polyol and a fatty acid(s) is not limited, and the fatty acid(s) may be linked to only one hydroxyl group. The fatty acid(s) may be linked to plural hydroxyl groups, but not all hydroxyl groups. Examples include monoesters, in which 1 fatty acid is attached to a polyol, diesters, in which 2 fatty acids are attached to a polyol, and triesters, in which 3 fatty acids are attached to a polyol. In an ester compound in which plural fatty acids are linked to one molecule of a polyol, the plural fatty acids may be the same fatty acid or different fatty acids may be linked.

The compositions comprising an ester compound of a polyol and a fatty acid as an active ingredient comprise 45 (w/v) % or more, preferably 50 (w/v) % or more, more preferably 60 (w/v) % or more, more preferably 70 (w/v) % or more, more preferably 80 (w/v) % or more, more preferably 90 (w/v) % or more, and particularly preferably 95 (w/v) % or more of the ester compound of a polyol and a fatty acid and may comprise 100 (w/v) % of the ester compound.

Examples of the ester compound include fatty acid esters of glycerol (monoglyceride), fatty acid esters of polyglycerol such as fatty acid esters of diglycerol and fatty acid esters of triglycerol, fatty acid esters of propylene glycol, fatty acid esters of sorbitan, and fatty acid esters of sucrose. More specifically, examples include glycerol caprylate, glycerol caprate, glycerol laurate, glycerol myristate, glycerol palmitate, glycerol stearate, glycerol behenate, diglycerol caprylate, diglycerol caprate, diglycerol laurate, diglycerol myristate, diglycerol palmitate, diglycerol stearate, diglycerol behenate, triglycerol caprylate, triglycerol caprate, triglycerol laurate, triglycerol myristate, triglycerol palmitate, triglycerol stearate, triglycerol behenate, tetraglycerol caprylate, tetraglycerol caprate, tetraglycerol laurate, tetraglycerol myristate, tetraglycerol palmitate, tetraglycerol stearate, tetraglycerol behenate, decaglycerol caprylate, decaglycerol caprate, decaglycerol laurate, decaglycerol myristate, decaglycerol palmitate, decaglycerol stearate, decaglycerol behenate, sucrose caprylate, sucrose caprate, sucrose laurate, sucrose myristate, sucrose palmitate, sucrose stearate, and sucrose behenate.

The ester compound of a polyol and a fatty acid or a composition comprising the ester compound has a function of a surfactant and may also be referred to as an ester-type non-ionic surfactant or a polyol-type surfactant. The ester compound of a polyol and a fatty acid or a composition comprising the ester compound as an active ingredient has a function of an emulsifier and commercially available emulsifiers may be used.

Examples of emulsifiers containing such an ester compound of a polyol and a fatty acid include the following. In the following description, the type of an ester compound is written in parentheses after the trade name of each emulsifier and the emulsifier contains the ester compound in the parenthesis most. The content (w/v)) of the ester compound is 45% or more, preferably 80% or more, more preferably 85% or more, more preferably 90% or more, and more preferably 95% or more.

Ester compounds of a fatty acid and glycerol include food emulsifiers such as EMULSY P-100 (monoglycerol palmitate and monoglycerol stearate), POEM M-100 (glycerol monocaprylate), POEM M-200 (glycerol monocaprate), POEM M-300 (glycerol monolaurate), POEM V-100 (glycerol monostearate), RIKEMAL B-100 (glycerol monobehenate), POEM V-200 (glycerol mono/distearate), POEM B-200 (glycerol mono/dibehenate), POEM DL-100 (diglycerol monolaurate), POEM DM-100 (diglycerol monomyristate), POEM DS-100A (diglycerol monostearate), POEM DP-95RF (diglycerol palmitate), RIKEMAL L-71-D (diglycerol laurate), RIKEMAL S-71-D (diglycerol stearate), POEM TRP-97RF (triglycerol monopalmitate), POEM J-4081V (tetraglycerol stearate), POEM J-0021 (decaglycerol laurate), and POEM J-0081HV (decaglycerol stearate) (all from Riken Vitamin Co., Ltd.), and RYOTO® Polyglyester SWA-15D (polyglycerol stearate), RYOTO® Polyglyester S-28D (polyglycerol stearate), RYOTO® Polyglyester S-24D (polyglycerol stearate), RYOTO® Polyglyester SWA-20D (polyglycerol stearate), RYOTO®

Polyglyester SWA-10D (polyglycerol stearate), RYOTO® Polyglyester CE-19D (polyglycerol caprylate), RYOTO® Polyglyester CA-F4 (polyglycerol laurate), RYOTO® Polyglyester L-10D (polyglycerol laurate), RYOTO® Polyglyester M-10D (polyglycerol myristate), RYOTO® Polyglyester O-50D (polyglycerol oleate), RYOTO® Polyglyester O-15D (polyglycerol oleate), RYOTO® Polyglyester B-100D (polyglycerol behenic acid ester), and RYOTO® Polyglyester B-70D (polyglycerol behenic acid ester) (all from Mitsubishi-Kagaku Foods Corporation), which are fatty acid esters of glycerol or fatty acid esters of polyglycerol.

Examples of the ester compounds of a fatty acid and propylene glycol include food emulsifiers such as RIKEMAL PL-100 (propylene glycol monolaurate), RIKEMAL PP-100 (propylene glycol monopalmitate), RIKEMAL PS-100 (propylene glycol monostearate), and RIKEMAL PB-100 (propylene glycol monobehenate) (all from Riken Vitamin Co., Ltd.).

Examples of ester compounds of a fatty acid and sorbitan include food emulsifiers such as RIKEMAL L-250A (sorbitan laurate), RIKEMAL P-300 (sorbitan palmitate), POEM S-60V (sorbitan stearate), POEM S-65V (sorbitan tristearate), RIKEMAL B-150 (sorbitan tribehenate), RIKEMAL C-250 (sorbitan caprate) (all from Riken Vitamin Co., Ltd.).

Examples of ester compounds of a fatty acid and sucrose include food emulsifiers such as RYOTO® Sugar Ester S-1570 (sucrose stearate), RYOTO® Sugar Ester O-1570 (sucrose oleate), RYOTO® Sugar Ester S-1670 (sucrose stearate), RYOTO® Sugar Ester P-1570, P-1670 (sucrose palmitate), RYOTO® Sugar Ester M-1695 (sucrose myristate), RYOTO® Sugar Ester L-1695 (sucrose laurate), and RYOTO® Sugar Ester B-370 (sucrose behenate) (all from Mitsubishi-Kagaku Foods Corporation).

Examples of food emulsifiers in which an organic acid is linked to a polyol include POEM W-60 (diacetyltartaric fatty acid monoglyceride), POEM B-15V and POEM BS-20 (succinic fatty acid monoglyceride), and POEM K-30 (citric fatty acid monoglyceride) (all from Riken Vitamin Co., Ltd.).

The lactic acid bacterium whose immunopotentiating activity is increased by a method for increasing the immunopotentiating activity of a lactic acid bacterium according to the present invention is a lactic acid bacterium that intrinsically has the immunopotentiating activity even in the absence of the composition according to the present invention. The phrase "has the immunopotentiating activity" means that the lactic acid bacterium has the effect on immunocompetent cells that are interferon-producing cells and promote their interferon production in vivo and in vitro. The immunopotentiating activity may also be referred to as interferon production-inducing activity. The immunocompetent cells include splenocytes and bone marrow cells. Particular examples of the immunocompetent cells include plasmacytoid dendritic cells (pDCs).

Interferons include Type I interferons, Type II interferons, and Type III interferons. Type I interferons are cytokines considered to be effective against viral infections and include interferon-α (1, 2, 4, 5, 6, 7, 8, 10, 13, 14, 16, 17, 21) and interferon-β. Type II interferons include interferon-γ and Type III interferons include interferon-λ. In particular, lactic acid bacteria having the inducibility of the production of Type I and Type III interferons and particularly the inducibility of the production of interferon-α, a Type I interferon, are preferred.

Furthermore, smaller lactic acid bacteria are preferred among lactic acid bacteria. Examples include lactic acid bacteria having a cell diameter of 5 μm or less, preferably 2 μm or less, and more preferably 1 μm or less.

Examples of lactic acid bacteria having the inducibility of the interferon production include lactic acid cocci of the genus *Lactococcus*, the genus *Leuconostoc*, the genus *Pediococcus*, the genus *Streptococcus*, the genus *Lactobacillus*, and the genus *Enterococcus*.

Such lactic acid bacteria include, but are not limited to, lactic acid bacteria that can promote the interferon production from plasmacytoid dendritic cells (pDCs).

Examples of the lactic acid bacteria that can activate plasmacytoid dendritic cells (pDCs) and promote the interferon production from pDCs include preferably lactic acid cocci, and more preferably, those in the genus *Lactococcus*, the genus *Leuconostoc*, the genus *Pediococcus*, and the genus *Streptococcus*. More particularly, examples include *Lactococcus garvieae*, *Lactococcus lactis* subsp. *cremoris*, *Lactococcus lactis* subsp. *lactis*, *Lactococcus lactis* subsp. *hordniae*, *Leuconostoc lactis*, *Pediococcus damnosus*, and *Streptococcus thermophilus*. When plasmacytoid dendritic cells are activated by lactic acid bacteria, cell projections, the characteristic of activated dendritic cells appear and the cells produce Type I and Type III interferons.

Specific examples of such lactic acid bacterial strains include *Lactococcus garvieae* NBRC100934, *Lactococcus lactis* subsp. *cremoris* JCM16167, *Lactococcus lactis* subsp. *cremoris* NBRC100676, *Lactococcus lactis* subsp. *hordniae* JCM1180, *Lactococcus lactis* subsp. *hordniae* JCM11040, *Lactococcus lactis* subsp. *lactis* NBRC12007, *Lactococcus lactis* subsp. *lactis* NRIC1150, *Lactococcus lactis* subsp. *lactis* JCM5805, *Lactococcus lactis* subsp. *lactis* JCM20101, *Leuconostoc lactis* NBRC12455, *Leuconostoc lactis* NRIC1540, *Pediococcus damnosus* JCM5886, *Streptococcus thermophilus* TA-45. Among these, *Lactococcus lactis* subsp. *lactis*, which is a coccus having a particularly high inducibility of the interferon-α production, may be used. Furthermore, *Lactococcus lactis* subsp. *lactis* JCM5805 and *Lactococcus lactis* subsp. *lactis* JCM20101 and particularly *Lactococcus lactis* JCM5805 may be preferably used.

Examples of lactic acid bacteria in the genus *Lactobacillus* include *Lactobacillus brevis* subsp. *coagulans* (JP Patent Publication (Kokai) No. 6-206826 A (1994)) and examples of specific strains include *Lactobacillus brevis* subsp. *Coagulans* KB290. Examples of lactic acid bacteria in the genus *Enterococcus* include *Enterococcus faecalis* and examples of specific strains include *Enterococcus faecalis* NF-1011, *Enterococcus faecalis* FK-23, and *Enterococcus faecalis* NT.

Furthermore, lactic acid bacteria having the interferon-inducing activity to the living body even when orally administered is preferred for increasing the immunopotentiating activity of the lactic acid bacteria with an immunopotentiating activity-increasing composition of the present invention. The aforementioned *Lactococcus lactis* JCM5805 can exhibit a high interferon production-inducing activity to the living body also when administered orally.

Furthermore, bacterial strains equivalent with *Lactococcus garvieae* NBRC100934, *Lactococcus lactis* subsp. *cremoris* JCM16167, *Lactococcus lactis* subsp. *cremoris* NBRC100676, *Lactococcus lactis* subsp. *hordniae* JCM1180, *Lactococcus lactis* subsp. *hordniae* JCM11040, *Lactococcus lactis* subsp. *lactis* NBRC12007, *Lactococcus lactis* subsp. *lactis* NRIC1150, *Lactococcus lactis* subsp. *lactis* JCM5805, *Lactococcus lactis* subsp. *lactis*

JCM20101, *Leuconostoc lactis* NBRC12455, *Leuconostoc lactis* NRIC1540, *Pediococcus damnosus* JCM5886, *Streptococcus thermophilus* TA-45, *Lactobacillus brevis* subsp. *Coagulans* KB290, *Enterococcus faecalis* NF-1011, *Enterococcus faecalis* FK-23, *Enterococcus faecalis* NT can be used. The term "strains equivalent" refers to strains derived from the aforementioned strains or strains which the aforementioned strains are derived from or progeny strains thereof. The equivalent strains may be stored in other strain preservation organization.

The immunopotentiating activity of a lactic acid bacterium can be increased by adding a lactic acid bacterial immunopotentiating activity-increasing composition according to the present invention to the lactic acid bacterium to contact them with each other, and then washing the lactic acid bacterium to remove the lactic acid bacterial immunopotentiating activity-increasing composition.

In order to contact the lactic acid bacterial immunopotentiating activity-increasing composition with the lactic acid bacterium, the lactic acid bacterium may be cultured in the presence of the lactic acid bacterial immunopotentiating activity-increasing composition or the lactic acid bacterial immunopotentiating activity-increasing composition may be added to a liquid containing the lactic acid bacterium. Both of the lactic acid bacterium and the lactic acid bacterial immunopotentiating activity-increasing composition may be also contained in a composition and may be stored in this condition at room temperature or by refrigeration or freezing. The contact between the lactic acid bacterium and the lactic acid bacterial immunopotentiating activity-increasing composition may be kept at room temperature to 60° C. for 10 minutes to 48 hours, preferably for 15 minutes to several hours, and further preferably for 20 minutes to 2 hours.

The washing may be conducted by repeating 1 to several times of adding water, physiological saline, phosphate buffered saline, or a buffer solution to the mixture of the lactic acid bacterium and the lactic acid bacterial immunopotentiating activity-increasing composition, mixing them, then conducting centrifugation, and discarding the supernatant.

Lactic acid bacterial immunopotentiating activity-increasing compositions according to the present invention may be used at such a concentration that the ratio of the concentration of the composition to the concentration of the lactic acid bacterium is 0.002 to 8:1, preferably 0.004 to 8:1, and more preferably 0.02 to 8:1. The concentration of lactic acid bacterium may be expressed as the weight of the lactic acid bacterium (dry weight)/the volume of liquid containing the lactic acid bacterium (w/v) and the weight of the lactic acid bacterium may be measured after centrifuging a suspension of the lactic acid bacterium to precipitate the lactic acid bacterium and drying the precipitate. For example, 1 mg/ml to 100 mg/ml (0.1 (w/v) % to 10 (w/v) %) of the lactic acid bacterium and 0.05 mg/ml to 50 mg/ml (0.005 (w/v) % to 5 (w/v) %) of the lactic acid bacterial immunopotentiating activity-increasing composition may be mixed. Preferably, 2.5 mg/ml to 50 mg/ml of the lactic acid bacterium and 0.1 to 20 mg/ml of the lactic acid bacterial immunopotentiating activity-increasing composition may be mixed.

In methods for increasing immunopotentiating activity of a lactic acid bacterium, comprising contacting a lactic acid bacterium with a lactic acid bacterial immunopotentiating activity-increasing composition according to the present invention, the concentration ratio of the lactic acid bacterium and the lactic acid bacterial immunopotentiating activity-increasing composition that can increase the immunopotentiating activity of the lactic acid bacterium is very large and a lactic acid bacterium having increased immunopotentiating activity can be obtained without strict adjustment of their mixing ratio.

Confirmation that no lactic acid bacterial immunopotentiating activity-increasing composition is mixed in a composition containing a lactic acid bacterium after washing can be made by measuring the number of the lactic acid bacteria per weight in the lactic acid bacterial composition after washing and comparing the number with that of the lactic acid bacterium that has not been contacted with the lactic acid bacterial immunopotentiating activity-increasing composition. If the number of the lactic acid bacteria per weight is equal to that of the lactic acid bacterium that has not been contacted with the lactic acid bacterial immunopotentiating activity-increasing composition, then it can be determined that the lactic acid bacterial immunopotentiating activity-increasing composition was removed by washing.

The immunopotentiating activity of a small amount of lactic acid bacteria can be increased by methods for increasing immunopotentiating activity of a lactic acid bacterium according to the present invention. As a result, an equivalent immunopotentiating effect can be obtained with a smaller amount of the lactic acid bacterium, relative to the immunopotentiating effect obtained by using the lactic acid bacterium whose immunopotentiating activity is not increased by the methods according to the present invention.

The lactic acid bacterium whose immunopotentiating activity is increased acts on immunocompetent cells that are interferon-producing cells contained in intestinal cells, bone marrow cells, or splenocytes and promotes the interferon production from the cells. As a result, the production of any of Type I interferons, Type II interferons, and Type III interferons may be promoted. Particularly, the production of Type I interferons and, more particularly, that of interferon-α are promoted. The production of Type II interferons such as interferon-γ from NK and Th1 cells can be also promoted by methods for increasing immunopotentiating activity of a lactic acid bacterium according to the present invention. The promotion of the interferon production increases the immune activity in the living body. Moreover, methods for increasing immunopotentiating activity of a lactic acid bacterium according to the present invention can promote the production of both of Type I and Type III interferons simultaneously, that is to say, they can promote the production of interferon-α, interferon-β, and interferon-γ, simultaneously. Furthermore, methods for increasing immunopotentiating activity of a lactic acid bacterium according to the present invention can activate plasmacytoid dendritic cells (pDCs). When plasmacytoid dendritic cells are activated, cell projections characteristic of activated dendritic cells appear and the cells produce Type I and Type III interferons.

The present invention also relates to a method for producing a lactic acid bacterium having increased immunopotentiating activity, comprising contacting a lactic acid bacterial immunopotentiating activity-increasing composition comprising an ester compound of a polyol and a fatty acid with a lactic acid bacterium and then washing the lactic acid bacterium to remove the ester compound of a polyol and a fatty acid. The obtained lactic acid bacterium does not contain the ester compound of a polyol and a fatty acid.

Whether the immunopotentiating activity of a lactic acid bacterium is increased by a method for increasing the immunopotentiating activity of a lactic acid bacterium according to the present invention can be determined by culturing the lactic acid bacterium in the presence of the lactic acid bacterial immunopotentiating activity-increasing composition, then washing the lactic acid bacterium, mixing the washed lactic acid bacterium and immunocompetent cells that are interferon-producing cells, and measuring the interferon production from the immunocompetent cells to determine whether it has been promoted in comparison with that using the lactic acid bacterium not cultured in the presence of the lactic acid bacterial immunopotentiating activity-increasing composition. The increase in the interferon production may be evaluated by measuring, for example, the amount of interferon in the culture medium by ELISA. When the immunopotentiating activity of a lactic acid bacterium is increased by a method for increasing the immunopotentiating activity of a lactic acid bacterium according to the present invention, the amount of the production of interferon-α from interferon-producing cells is increased by 10% or more, preferably 20% or more, more preferably 40% or more, or most preferably 80% or more by the lactic acid bacterium whose immunopotentiating activity is increased. The degree of the increase may be indicated, for example, by the concentration of interferon-α in the lactic acid bacterial medium when the amount of interferon-α produced is measured in vitro.

The lactic acid bacterium whose immunopotentiating activity is increased by a method for increasing the immunopotentiating activity of a lactic acid bacterium according to the present invention may be used as a medicine for inducing the production of interferon and increasing the immune activity in the living body. That is to say, the lactic acid bacterium whose immunopotentiating activity is increased by the method for increasing the immunopotentiating activity of a lactic acid bacterium may be used as an immunoadjuvant or a composition containing lactic acid bacterium such as an immunopotentiating agent. Such a medicine may be used as a prophylactic or therapeutic agent for cancers including kidney cancer, multiple myeloma, chronic myelogenous leukemia, hairy cell leukemia, glioblastoma, medulloblastoma, astrocytoma, malignant melanoma, mycosis fungoides, and adult T cell-leukemia; viral infections including subacute sclerosing panencephalitis, HTLV-1 myelopathy, hepatitis B, and hepatitis C; bacterial infections such as *Chlamydia* (venereal disease), Mycobacteria (tuberculosis), *Listeria* (sepsis), *Staphylococcus* (food poisoning), and *Helicobacter* (gastritis); and autoimmune diseases including multiple sclerosis, which have been already known as adaptation diseases of Type I interferons. The medicine is particularly useful as preventive and therapeutic agents against viral infections. The medicine may also be used as a prophylactic or therapeutic agent for osteoporosis since Type I interferons are known to have the function of inhibiting differentiation from osteoblasts to osteoclasts as their activity.

Furthermore, lactic acid bacterial strains whose immunopotentiating activity is increased by a method for increasing the immunopotentiating activity of a lactic acid bacterium according to the present invention may be used as vaccine by expressing an antigen corresponding to a certain disease in the strain using a genetic technique. Such xenogeneic antigen-expressing strains are particularly suitable as a host for the oral vaccine since the cell wall of lactic acid bacteria serves to protect the antigen from gastric acid. Vaccines generally include live vaccines, inactivated whole virion vaccines, and split vaccines. However, live vaccines has a risk of reversion to pathogenic viruses, inactivated whole virion vaccines may cause side effects of impurities, and split vaccines, which are the safest, have problems of efficacy. To overcome such problems, recombinant vaccines expressing only the antigen of interest have been developed. The expression of antigen in lactic acid bacteria whose immunopotentiating activity is increased by a method for increasing immunopotentiating activity of a lactic acid bacterium according to the present invention would produce the adjuvant effect as well and be very useful.

The form of the composition containing a lactic acid bacteria whose immunopotentiating activity is increased by a method for increasing immunopotentiating activity of a lactic acid bacterium according to the present invention is not particularly limited. Examples include powder, granules, tablets, syrups, injections, drops, powdered drugs, suppositories, suspensions, and ointments. Pharmaceutical compositions according to the present invention may be orally administered or may be parenterally administered, such as by intravenous injection, intramuscular injection, subcutaneous administration, rectal administration, or transdermal administration, but oral administration is preferred. The aforementioned interferon production-inducing agent may contain an excipient, a disintegrator, a binder, a lubricant, and/or a colorant. Examples of the excipient include glucose, lactose, cornstarch, and Sorbit. Examples of the disintegrator include starch, sodium alginate, gelatin powder, calcium carbonate, calcium citrate, and dextrin. Examples of the binder include dimethylcellulose, polyvinyl alcohol, polyvinyl ether, methylcellulose, ethyl cellulose, Arabian gum, gelatin, hydroxypropyl cellulose, and polyvinylpyrrolidone. Examples of lubricants include talc, magnesium stearate, polyethyleneglycol, and hydrogenated vegetable oils. The dose may be determined as appropriate according to the age, body weight, sex of the patient receiving administration, difference of disease, and degrees of symptoms and administered once a day or several divided doses may be administered daily. An amount of culture corresponding to $1 \times 10^9$ to $1 \times 10^{12}$ cells per dose may be administered. Alternatively, 1 to 1000 mg in terms of the weight of lactic acid bacteria per dose may be administered.

Furthermore, lactic acid bacteria whose immunopotentiating activity is increased by a method for increasing immunopotentiating activity of a lactic acid bacterium according to the present invention may be used in a beverage or food. The inclusion of such a lactic acid bacterium in a beverage or food allows use of the beverage or food as a beverage or food for inducing the interferon production, an immunopotentiating beverage or food, an immunostimulatory beverage or food or a beverage or food for preventing viral infection. Examples of the beverages and foods for the purpose include milk and dairy products; beverages, seasonings; alcoholic beverages; processed agricultural and forest foods; confectioneries and breads; grain flours and noodles; processed marine products; processed live stock products; oils and fats and processed oils and fats; frozen cooked foods; retort foods; instant foods, and food materials. In particular, the lactic acid bacteria can be used in fermented dairy products such as yogurts and cheeses and lactic fermented beverages. When used in a fermented beverage or food, a required amount of lactic acid bacteria having immunopotentiating activity may be added to the fermented beverage or food as a dead bacteria or may be used as lactic acid bacteria starter to produce a fermented beverage or food.

Beverages and foods according to the present invention include health beverages and foods, beverages and foods for specific health uses, functional nutritional beverages and foods, and beverage or food supplements. As used herein, the term "beverages and foods for specified health uses" refers to beverages and foods that are taken for a specific health purpose in diets and have an indication that the health purpose may be achieved by the intake. These beverages and foods may have an indication, for example, that it increases the immune function of the body; activates the immune function of the body; reduces the possibility of catching a cold; reduces the possibility of being infected with viruses such as influenza virus, norovirus, or rotavirus; or has a cancer-preventing effect.

EXAMPLES

The present invention will be specifically described by the following Examples, but the present invention is not limited by these Examples.

Example 1

Ester Compound of Polyol and Fatty Acid, which has Hydrophobic Group. First Evaluation of Concentration.
<Method>
A glycerol stock of lactic acid bacteria (the strain JCM5805) was thawed and cultured in MRS medium. The cultured lactic acid bacteria (the strain JCM5805) were washed with pure water and concentrated 20 times and then the bacteria were mixed with ester compound of polyol and fatty acid, which has hydrophobic group (RYOTO Sugar Ester P-1670) at the concentrations set forth in Table 1 at a ratio of 1:19 to obtain bacteria concentration of 2.5 mg/ml, which is the same as that at the end of this culturing. After mixing the lactic acid bacteria and the ester compound of polyol and fatty acid, which has hydrophobic group for 30 minutes, the mixture was concentrated 20 times by centrifugation and the supernatant was discarded. Pure water was added to have a bacterial cell concentration of 2.5 mg/ml again to wash the cells. The mixture was concentrated 20 times by centrifugation and the supernatant was discarded. Pure water was added and the cells were suspended at 50 mg/ml. The suspension was subjected to sterilization at 105° C. for 30 minutes. After the end of the sterilization, the suspension was centrifuged and the supernatant was discarded and the precipitates were freeze-dried.

TABLE 1

| | Lactic acid bacterial concentration (mg/ml) | Emulsifier concentration (mg/ml) | Lactic acid bacterium:Emulsifier |
|---|---|---|---|
| (1) | 2.5 | 0 | 1:0 |
| (2) | 2.5 | 1 | 1:0.4 |
| (3) | 2.5 | 5 | 1:2 |
| (4) | 2.5 | 10 | 1:4 |
| (5) | 2.5 | 20 | 1:8 |

Figure 1:
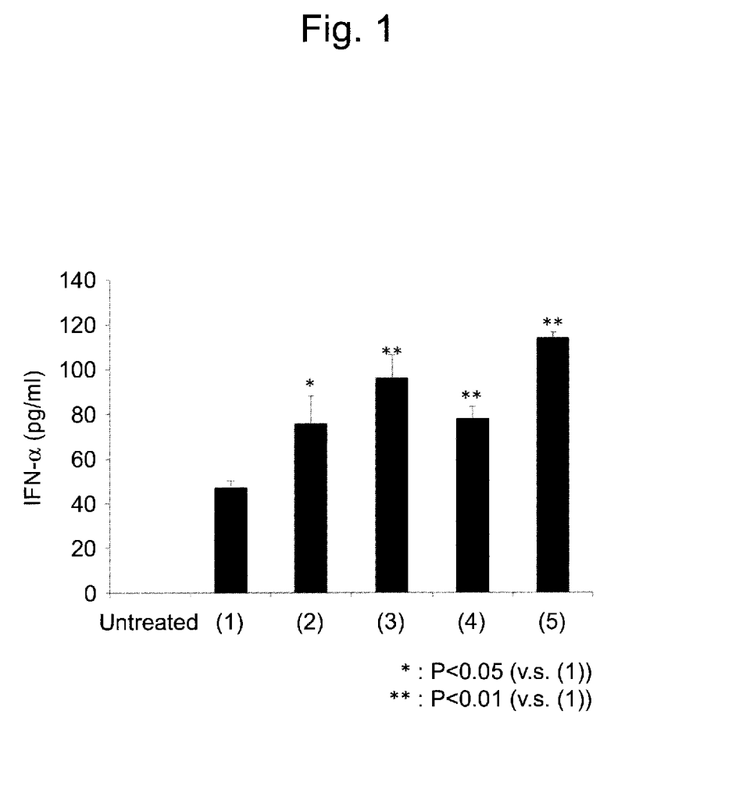
FIG. 1 illustrates an effect of inducing interferon-a production at varying relative concentrations of an ester compound of a polyol and a fatty acid to a lactic acid bacterium (Part 1).

Splenocytes were collected from female 129/SV mice according to a usual method and erythrocytes were removed. The obtained splenocytes were suspended at $4\times10^6$ cells/ml in RPMI medium (Sigma-Aldrich Co. LLC) containing 10% FBS and 50 µM β-mercaptoethanol. The prepared lactic acid bacteria (the strain JCM5805) were added to 500 µl of the obtained cell suspension at a final concentration of 10 µg/ml. The resulting mixture was cultured at 37° C., 5% $CO_2$ in a $CO_2$ incubator. The culture supernatant was collected 24 hours later and the concentration of interferon-α was measured by an interferon-α assay kit (PBL Assay Science).
<Result>
Results are illustrated in FIG. 1. JCM5805 which have not treated with the ester compound constituted by polyol which have hydrophobic group, and fatty acid exhibited the interferon-α inducing activity. JCM5805 which were mixed with 1 to 20 mg/ml of the ester compound of polyol and fatty acid, which has hydrophobic group (RYOTO Sugar Ester P-1670) exhibited the higher interferon-α inducing activity compared to JCM5805 which have not treated with the ester compound of polyol and fatty acid, which has hydrophobic group. This result revealed that the immunopotentiating activity of the strain JCM5805 is increased by mixing with the range of 1 to 20 mg/ml of ester compound of polyol and fatty acid, which has hydrophobic group (RYOTO Sugar Ester P-1670) when JCM5805 is prepared. Moreover, the remaining amount of the ester compound of polyol and fatty acid, which has hydrophobic group (RYOTO Sugar Ester P-1670) was examined by measuring the number of the bacteria per weight of the powder produced. Since the numbers of bacteria per weight had no difference as illustrated in Table 2, it was found that the ester compound of a polyol and a fatty acid, which has hydrophobic group was not remained.

TABLE 2

| | Number of bacteria per weight ($\times10^9$ cells/mg) | S.D. | Number of bacteria per weight (theoretical value) without washing out of emulsifier ($\times10^9$ cells/mg) |
|---|---|---|---|
| (1) | 3.48 | 0.006 | 3.48 |
| (2) | 3.45 | 0.040 | 2.48 |
| (3) | 3.08 | 0.021 | 1.16 |
| (4) | 3.32 | 0.031 | 0.70 |
| (5) | 3.37 | 0.061 | 0.39 |

Example 2

Ester Compound of Polyol and Fatty Acid, which has Hydrophobic Group. Second Evaluation of Concentration.
<Method>
A glycerol stock of lactic acid bacteria (the strain JCM5805) was thawed and cultured in MRS medium. The cultured lactic acid bacteria (the strain JCM5805) were washed with pure water and then the bacteria were mixed with ester compound of polyol and fatty acid, which has hydrophobic group (RYOTO Sugar Ester P-1670) at the concentrations set forth in Table 3 at a ratio of 1:19 to obtain bacteria concentration of 2.5 mg/ml, which is the same as that at the end of this culturing. After mixing the lactic acid bacteria and the ester compound of polyol and fatty acid, which has hydrophobic group for 30 minutes, the mixture was concentrated 20 times by centrifugation and the supernatant was discarded. Pure water was added to have a bacterial cell concentration of 2.5 mg/ml again to wash the cells. The mixture was concentrated 20 times by centrifugation and the supernatant was discarded. Pure water was added and the cells were suspended at 50 mg/ml. The suspension was subjected to sterilization at 105° C. for 30 minutes. After the end of the sterilization, the suspension was centrifuged and the supernatant was discarded and the precipitates were freeze-dried.

TABLE 3

| | Lactic acid bacterial concentration (mg/ml) | Emulsifier concentration (mg/ml) | Lactic acid bacterium:Emulsifier |
|---|---|---|---|
| (1) | 2.5 | 0 | 1:0 |
| (2) | 2.5 | 0.01 | 1:0.004 |
| (3) | 2.5 | 0.1 | 1:0.04 |

TABLE 3-continued

| | Lactic acid bacterial concentration (mg/ml) | Emulsifier concentration (mg/ml) | Lactic acid bacterium:Emulsifier |
|---|---|---|---|
| (4) | 2.5 | 0.5 | 1:0.2 |
| (5) | 2.5 | 1 | 1:0.4 |
| (6) | 2.5 | 5 | 1:2 |

Figure 2:
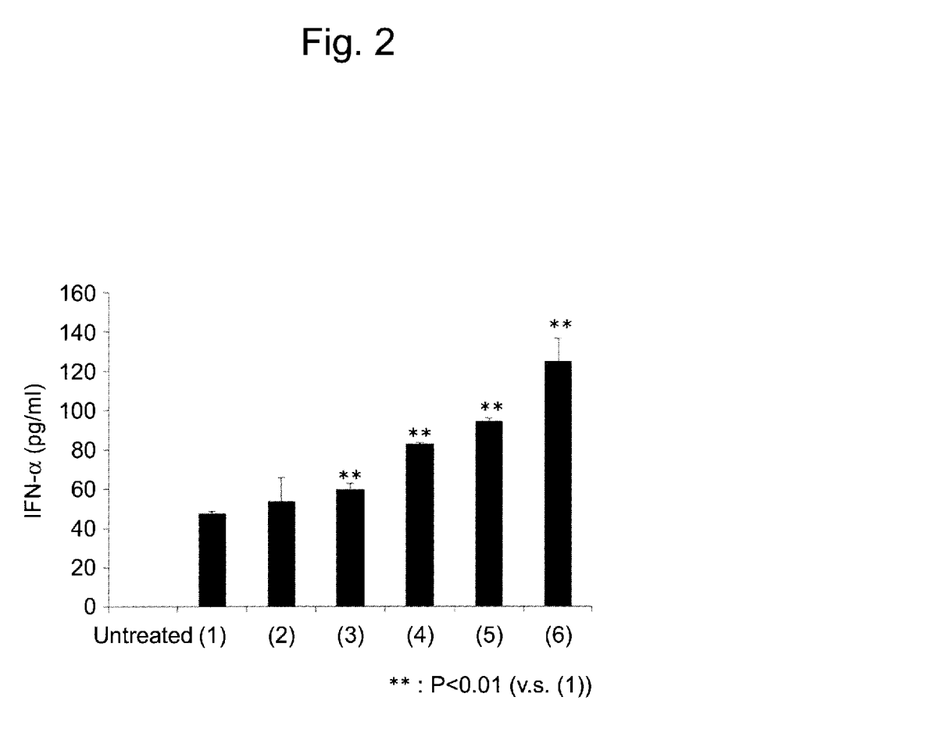
FIG. 2 illustrates an effect of inducing interferon-α production at varying relative concentrations of an ester compound of a polyol and a fatty acid to a lactic acid bacterium (Part 2).

Splenocytes were collected from female 129/SV mice according to a usual method and erythrocytes were removed. The obtained splenocytes were suspended at $4 \times 10^6$ cells/ml in RPMI medium (Sigma-Aldrich Co. LLC) containing 10% FBS and 50 µM β-mercaptoethanol. The prepared lactic acid bacteria (the strain JCM5805) were added to 500 µl of the obtained cell suspension to have a final concentration of 10 µg/ml. The resulting mixture was cultured at 37° C., 5% $CO_2$ in a $CO_2$ incubator. Culture supernatants were collected 24 hours later and the concentration of interferon-α was measured by an interferon-α assay kit (PBL Assay Science).
<Result>
Results are illustrated in FIG. 2. JCM5805 which have not treated with the ester compound of polyol and fatty acid, which has hydrophobic group exhibited the interferon-α inducing activity. JCM5805 which have treated with 0.1 to 5 mg/ml of the ester compound of polyol and fatty acid, which has hydrophobic group (RYOTO Sugar Ester P-1670) exhibited higher interferon-α inducing activity compared to JCM5805 which were not treated with the ester compound of polyol and fatty acid, which has hydrophobic group. JCM5805 which have treated with 0.1 mg/ml of the esters did not exhibit significantly higher interferon-α inducing activity compared to JCM5805 which have not treated with the ester compound of polyol and fatty acid, which has hydrophobic group. This result revealed that the immunopotentiating activity of the strain JCM5805 is increased by mixing with the range of 0.10 to 5 mg/ml of ester compound of polyol and fatty acid, which has hydrophobic group (RYOTO Sugar Ester P-1670) when JCM5805 is prepared. Moreover, the remaining amount of the ester compound of polyol and fatty acid, which has hydrophobic group was examined by measuring the number of the bacteria per weight of the powder produced. Since the numbers of bacteria per weight had no difference as illustrated in Table 4, it was found that the ester compound of a polyol and a fatty acid, which has hydrophobic groups was not remained.

TABLE 4

| | Number of bacteria per weight ($\times 10^9$ cells/mg) | S.D. | Number of bacteria per weight (theoretical value) without washing out of emulsifier ($\times 10^9$ cells/mg) |
|---|---|---|---|
| (1) | 3.97 | 0.09 | 3.97 |
| (2) | 4.11 | 0.07 | 3.95 |
| (3) | 4.07 | 0.05 | 3.82 |
| (4) | 3.69 | 0.02 | 3.31 |
| (5) | 3.67 | 0.07 | 2.84 |
| (6) | 3.82 | 0.02 | 1.32 |

Example 3

Study of Lactic Acid Bacterial Concentration
<Method>
A glycerol stock of lactic acid bacteria (the strain JCM5805) were thawed and cultured in MRS medium. The cultured lactic acid bacteria (the strain JCM5805) were washed with pure water and concentrated, and then the lactic acid bacteria were resuspended with a solution of ester compound of polyol and fatty acid, which has hydrophobic group (RYOTO Sugar Ester P-1670) at the concentrations set forth in Table 5 and prepared a suspension at a bacterial cell concentration of 50 mg/ml, which is 20 times of the concentration at the end of the culturing. The suspension was then subjected to sterilization at 105° C. for 30 minutes. After sterilization, pure water was added to have a bacterial cell concentration of 2.5 mg/ml. The ester compound of polyol and fatty acid, which has hydrophobic group was washed off by centrifuging the cell suspension and removing the supernatant, and the cells were freeze-dried.

TABLE 5

| | Lactic acid bacterial concentration (mg/ml) | Emulsifier concentration (mg/ml) | Lactic acid bacterium:Emulsifier |
|---|---|---|---|
| (1) | 50 | 0 | 1:0 |
| (2) | 50 | 1 | 1:0.02 |
| (3) | 50 | 5 | 1:0.1 |
| (4) | 50 | 10 | 1:0.2 |
| (5) | 50 | 20 | 1:0.4 |

Figure 3:
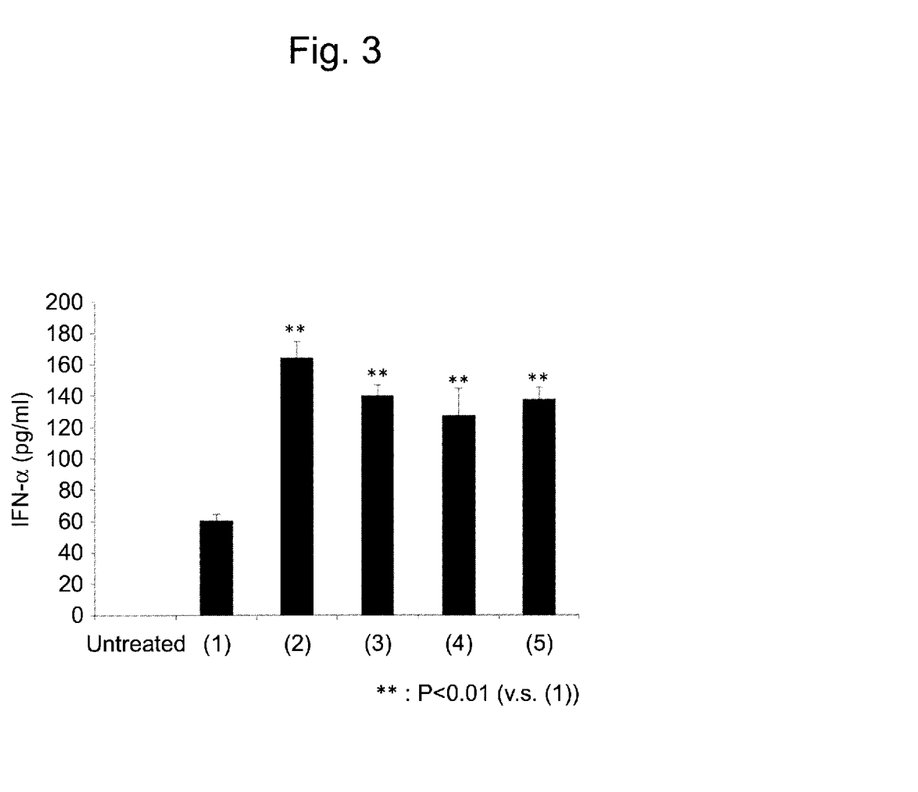
FIG. 3 illustrates an effect of inducing interferon-α production at varying relative concentrations of a lactic acid bacterium to an ester compound of a polyol and a fatty acid.

Splenocytes were collected from female 129/SV mice according to a usual method and erythrocytes were removed. The obtained splenocytes were suspended at $4 \times 10^6$ cells/ml in RPMI medium (Sigma-Aldrich Co. LLC) containing 10% FBS and 50 µM β-mercaptoethanol. The prepared lactic acid bacteria (the strain JCM5805) were added to 500 µl of the obtained cell suspension to have a final concentration of 10 µg/ml. The resulting mixture was cultured at 37° C., 5% $CO_2$ in a $CO_2$ incubator. The culture supernatant was collected 24 hours later and the concentration of interferon-α was measured by an interferon-α assay kit (PBL Assay Science).
<Result>
Results are illustrated in FIG. 3. JCM5805 which have not treated with the ester compound of polyol and fatty acid, which has hydrophobic group exhibited the interferon-α inducing activity. JCM5805 which have prepared by mixing 1 to 20 mg/ml of lactic acid bacteria with the ester compound of polyol and fatty acid, which has hydrophobic group exhibited higher interferon-α inducing activity compared to JCM5805 which have not treated with the ester compound of polyol and fatty acid, which has hydrophobic group. This result revealed that the immunopotentiating activity is increased by mixing lactic acid bacteria (the strain JCM5805) at a concentration of 50 mg/ml in the preparation of the lactic acid bacteria. Moreover, the remaining amount of the ester compound of a polyol and a fatty acid, which has hydrophobic groups was examined by measuring the number of the bacteria per weight of the powder produced. Since the numbers of bacteria per weight had no difference as illustrated in Table 6, it was found that the ester compound of a polyol and a fatty acid, which has hydrophobic groups was not remained.

TABLE 6

| | Number of bacteria per weight ($\times 10^9$ cells/mg) | S.D. | Number of bacteria per weight (theoretical value) without washing out of emulsifier ($\times 10^9$ cells/mg) |
|---|---|---|---|
| (1) | 3.35 | 0.06 | 3.35 |
| (2) | 3.10 | 0.012 | 3.28 |
| (3) | 3.17 | 0.006 | 3.04 |

TABLE 6-continued

| | Number of bacteria per weight ($\times 10^9$ cells/mg) | S.D. | Number of bacteria per weight (theoretical value) without washing out of emulsifier ($\times 10^9$ cells/mg) |
|---|---|---|---|
| (4) | 3.16 | 0.006 | 2.79 |
| (5) | 3.05 | 0.035 | 2.39 |

Example 4

Study with Ester Compound of Polyol and Fatty Acid, which has Hydrophobic Group.
<Method>
Lactic acid bacterial samples were prepared by mixing 2.5 mg/ml of ester compound of polyol and fatty acid showed in Table 7 with 1 mg/ml sterilized lactic acid bacteria (the strain JCM5805) for 30 minutes, then washing the bacteria with PBS to remove the ester compound of polyol and fatty acid, and resuspending the bacteria with PBS to have a 1 mg/ml of lactic acid bacteria.

TABLE 7

| (1) | Without treatment with ester compound of polyol and fatty acid (lactic acid bacteria only) |
| (2) | RYOTO Sugar Ester P-1670 |
| (3) | RYOTO Sugar Ester S-1670 |
| (4) | RYOTO Sugar Ester O-1570 |

Figure 4:
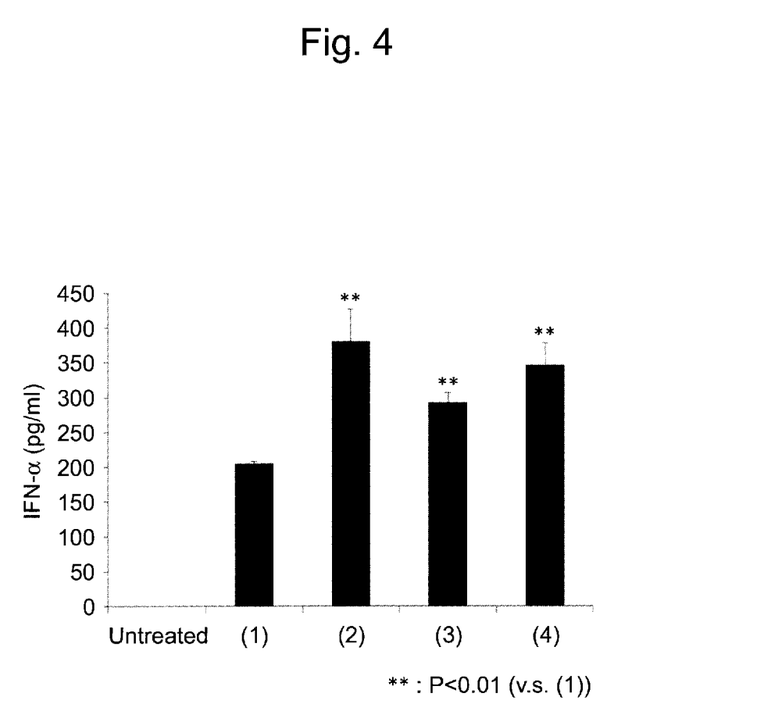
FIG. 4 illustrates a result of the study on the effect of ester compounds of a polyol and a fatty acid having different hydrophobic groups.

Bone marrow cells were collected from female 129/SV mice according to a usual method and erythrocytes were removed. The obtained bone marrow cells were suspended at $1 \times 10^6$ cells/ml in RPMI medium (Sigma-Aldrich Co. LLC) containing 10% FBS, 50 µM 3-mercaptoethanol, and 100 ng/ml murine Flt-3 ligand. A plate was inoculated with 1 ml of the obtained cell suspension and incubated at 37° C., 5% $CO_2$ in a $CO_2$ incubator for 1 week to induce bone marrow-derived dendritic cells. After 1 week of culturing, the lactic acid bacterial sample described above was added to the plate to have 10 µg/ml of lactic acid bacteria. The culture supernatant was collected 24 hours later and the concentration of interferon-α was measured by an interferon-α assay kit (PBL Assay Science).
<Result>
Results are illustrated in FIG. 4. Sample (1) (lactic acid bacteria (JCM5805) which have not treated with esters of polyol and fatty acid) exhibited the interferon-α inducing activity and any kind of ester compound (Sugar Ester P-1670 (sucrose palmitate), Sugar Ester S-1670 (sucrose stearate), Sugar Ester O-1570 (sucrose oleate)) further increased the interferon-α inducing activity. Accordingly, it was found that the hydrophobic moiety of ester compounds that increase the immunopotentiating activity of lactic acid bacteria is not limited to a specific hydrophobic group but may be any of various hydrophobic groups.

Example 5

Study with Ester Compound of Polyol and Fatty Acid, which has Different Hydrophilic Group.
<Method>
Lactic acid bacterial samples were prepared by mixing 2.5 mg/ml of ester compound of polyol and fatty acid showed in in Table 8 with 1 mg/ml sterilized lactic acid bacteria (the strain JCM5805) for 30 minutes, then washing the bacteria with PBS to remove the ester compound of polyol and fatty acid, and resuspending the bacteria with PBS to have a 1 mg/ml of lactic acid bacteria.

TABLE 8

| (1) | Without treatment with ester compound of polyol and fatty acid (lactic acid bacterium only) |
| (2) | RYOTO Polyglyester SWA-15D |
| (3) | RYOTO Polyglyester S-28D |

Figure 5:
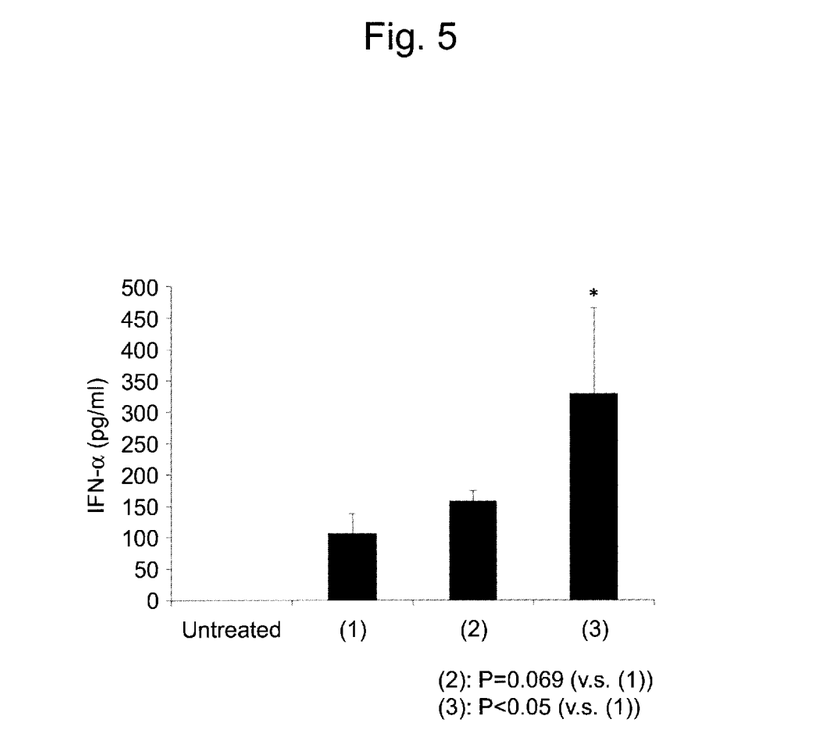
FIG. 5 illustrates a result of the study on the effect of ester compounds of a polyol and a fatty acid having different hydrophilic groups.

Bone marrow cells were collected from female 129/SV mice according to a usual method and erythrocytes were removed. The obtained bone marrow cells were suspended at $1 \times 10^6$ cells/ml in RPMI medium (Sigma-Aldrich Co. LLC) containing 10% FBS, 50 µM β-mercaptoethanol, and 100 ng/ml murine Flt-3 ligand. A plate was inoculated with 1 ml of the obtained cell suspension and incubated at 37° C., 5% $CO_2$ in a $CO_2$ incubator for 1 week to induce bone marrow-derived dendritic cells. After 1 week of culturing, the lactic acid bacterial sample described above was added to the plate to have 10 µg/ml of lactic acid bacteria. The culture supernatant was collected 24 hours later and the concentration of interferon-α was measured by an interferon-α assay kit (PBL Assay Science).
<Result>
Results are illustrated in FIG. 5. JCM5805 which have not treated with the ester compound of polyol and fatty acid exhibited the interferon-α inducing activity, any ester compound (Polyglyester SWA-15D (polyglycerol stearate) and Polyglyester S-28D (polyglycerol stearate)) further increased the interferon-α inducing activity. Accordingly, it was found that the hydrophilic moiety of ester compounds that increase the immunopotentiating activity of lactic acid bacteria is not limited to a specific hydrophilic group but may be any of various hydrophilic groups.

INDUSTRIAL AVAILABILITY

Lactic acid bacteria having an immunopotentiating activity increased by a method according to the present invention may be used as an active ingredient of compositions for increasing the immunopotentiating activity.

All publications, patents and patent applications cited herein shall be incorporated herein by reference as they are.

The invention claimed is:
1. A method of producing a lactic acid bacterium having an increased immunopotentiating activity comprising contacting a lactic acid bacterium having immunopotentiating activity with a lactic acid bacterial immunopotentiating activity-increasing composition comprising an ester compound of a polyol selected from the group consisting of monoglycerol, polyglycerol, and sucrose and a fatty acid selected from the group consisting of caprylic acid, capric acid, lauric acid, myristic acid, palmitic acid, stearic acid and behenic acid as an ingredient and keeping the contacted lactic acid bacterium at room temperature to 60° C. for 10 minutes to 48 hours and then washing the contacted lactic acid bacterium with water, physiological saline, phosphate buffered saline, or a buffer solution to remove the lactic acid bacterial immunopotentiating activity-increasing composition,
wherein the ratio of the concentration of the ester compound of the polyol and the fatty acid to the concentration of the lactic acid bacterium is in the range of 0.02 to 8:1 and wherein the lactic acid bacterium having the immunopotentiating activity is *Lactococcus lactis* JCM5805, wherein the increase in the immunopotentiating activity is determined by measuring the amount of interferon-alpha produced upon mixing the washed lactic acid bacterium with interferon-producing immunocompetent cells, wherein the amount of the interferon-alpha produced by the interferon-producing immunocompetent cells is increased by 10% or more compared to the lactic acid bacterium having the immunopotentiating activity that is not contacted with the lactic acid bacterial immunopotentiating activity-increasing composition.

2. The method of claim 1, wherein the contacting is by culturing the lactic acid bacterium having the immunopotentiating activity in the presence of the lactic acid bacterial immunopotentiating activity-increasing composition.

3. The method of claim 1, wherein the ester compound of the polyol and the fatty acid is not modified with any organic acid.

4. The method of claim 1, wherein the concentration of the lactic acid bacterium is 2.5 mg/ml to 50 mg/ml when the lactic acid bacterium is contacted with the lactic acid bacterial immunopotentiating activity-increasing composition.

5. The method of claim 1, wherein the concentration of the ester compound of the polyol and the fatty acid is 0.1 mg/ml to 20 mg/ml when the lactic acid bacterium is contacted with the lactic acid bacterial immunopotentiating activity-increasing composition.

6. The method of claim 1, wherein the polyol is polyglycerol or sucrose.

7. The method of claim 1, wherein the fatty acid is selected from the group consisting of palmitic acid, stearic acid, and oleic acid.

8. The method of claim 1, wherein the lactic acid bacterium is contacted with the lactic acid bacterial immunopotentiating activity-increasing composition for 20 minutes to 2 hours.

9. The method of claim 1, wherein the washing is by adding, one to several times, the water, the physiological saline, the phosphate buffered saline, or the buffer solution to the mixture of the lactic acid bacterium and the lactic acid bacterial immunopotentiating activity-increasing composition, then centrifuging, and discarding the supernatant.

* * * * *